United States Patent [19]

Heise et al.

[11] 4,426,538

[45] Jan. 17, 1984

[54] PROCESS FOR THE PREPARATION OF OPTIONALLY P-CHLORINE-SUBSTITUTED 2,6-DIAMINOTOLUENE

[75] Inventors: Klaus-Peter Heise, Bergisch-Gladbach; Ernst Schneider; Karlfried Wedemeyer, both of Cologne, all of Fed. Rep. of Germany

[73] Assignee: Bayer Aktiengesellschaft, Leverkusen, Fed. Rep. of Germany

[21] Appl. No.: 341,375

[22] Filed: Jan. 21, 1982

[30] Foreign Application Priority Data

Feb. 10, 1981 [DE] Fed. Rep. of Germany ....... 3104643

[51] Int. Cl.$^3$ ............................................. C07C 85/11
[52] U.S. Cl. .................................................. 564/417
[58] Field of Search ........................................ 564/417

[56] References Cited

U.S. PATENT DOCUMENTS

| | | | |
|---|---|---|---|
| 3,474,144 | 10/1969 | Craig et al. | 564/417 |
| 3,546,297 | 12/1970 | Kosak | 564/417 |
| 3,666,813 | 5/1972 | Hindin et al. | 564/417 |
| 3,683,025 | 8/1972 | Pons | 564/417 |
| 3,888,929 | 6/1975 | Rivier | 564/417 X |
| 3,989,756 | 11/1976 | Fujise et al. | 564/417 |
| 4,206,148 | 6/1980 | Biola et al. | 564/417 X |

OTHER PUBLICATIONS

"J. Ind. Chem. Soc.", No. 5, pp. 331 to 334, 1959.

*Primary Examiner*—Paul F. Shaver
*Attorney, Agent, or Firm*—Sprung, Horn, Kramer & Woods

[57] ABSTRACT

The invention relates to a process for the preparation of optionally p-chlorine-substituted 2,6-diaminotoluene, which is characterized in that 3,4-dichlorotoluene is dinitrated in the presence of an inert, water-immiscible, organic solvent and/or diluent at temperatures of $-10°$ to $+100°$ C. and is subsequently reduced, optionally after intermediate isolation of the dinitro compound, in the presence of an inert organic solvent and/or diluent and/or of water, with partial or complete splitting-off of the chlorine atoms, to give the diamino compound.

2,6-Diaminotoluenes are valuable intermediates for the preparation of diisocyanates and polyurethanes; the 2,6-diaminotoluene is furthermore used for the preparation of dyestuffs and antioxidants.

25 Claims, No Drawings

PROCESS FOR THE PREPARATION OF OPTIONALLY P-CHLORINE-SUBSTITUTED 2,6-DIAMINOTOLUENE

The present invention relates to a process for the preparation of optionally p-chlorine-substituted 2,6-diaminotoluene from 3,4-dichlorotoluene.

J. Chem. Soc. 79, 1122 (1901) discloses the dinitration of dichlorotoluene with a 7.7-fold excess of fuming nitric acid at 100° C. in the presence of concentrated sulphuric acid. To isolate the dinitro compounds, the reaction mixture is poured onto ice and, after filtration, the product is subjected to fractional crystallization from alcohol and glacial acetic acid.

Further, J. Ind. Chem. Soc., Vol. 33, No. 5, pages 331 and 334 (1959) discloses the dinitration of 3,4-dichlorotoluene with a mixture of sulphuric acid and nitric acid. According to this process, the reaction mixture is heated for several hours at 120° C. and is then poured onto ice, and the product which has precipitated is recrystallized by means of alcohol or acetic acid. 3,4-Dichloro-2,6-dinitrotoluene is obtained in 80% yield.

The nitration processes described have the disadvantage that drastic nitration conditions are employed, which have an adverse effect on the yield of the desired dinitro compound. To isolate the desired dinitro compound it is necessary, for example, to carry out an industrially expensive fractional crystallization with alcohol/acetic acid. Furthermore, the drastic nitration conditions can cause safety problems. In addition, the removal of the waste acid, which still contains large amounts of unconverted nitric acid, entails considerable expense in industrial operation, which very adversely affects the economics of the nitration process.

A process for the preparation of optionally p-chlorine-substituted 2,6-diaminotoluene has now been found, which is characterized in that 3,4-dichlorotoluene is dinitrated in the presence of an inert, water-immiscible, organic solvent and/or diluent at temperatures of $-10°$ to $+100°$ C. and is subsequently reduced, optionally after intermediate isolation of the dinitro compound, in the presence of inert organic solvents and/or diluents and/or of water, with partial or complete splitting-off of the chlorine atoms, to give the diamino compound.

According to the process of the invention, the nitration of the 3,4-dichlorotoluene is carried out in the presence of inert, water-immiscible, organic solvents and/or diluents. The solvents and/or diluents can be employed either individually or as mixtures with one another.

Suitable inert, water-immiscible, organic solvents and/or diluents are, for example, aliphatic or cycloaliphatic hydrocarbons with 5 to 20, preferably 6 to 15, carbon atoms, such as hexane, heptane, octane, decane, dodecane, decalin, cyclohexane and their isomers, preferably dodecane isomer mixtures and halogenated aliphatic hydrocarbons with 1 to 3 carbon atoms, such as methylene chloride, chloroform, carbon tetrachloride, dichloroethane, trichloroethane, dichloropropane or trichloropropane, preferably methylene chloride or dichloroethane.

The amount of the inert organic solvents and/or diluents can be varied within wide ranges. For example, when using methylene chloride 0.8 to 2.5 liters, preferably 1 to 2 liters, and when using dodecane 3 to 10 liters, preferably 4 to 7.5 liters, are employed, per kg of 3,4-dichlorotoluene, in the process according to the invention.

Nitrating agents used in the process according to the invention are, above all, mixtures of sulphuric acid and nitric acid, as well as mixtures of oleum and nitric acid. Furthermore, it is possible to carry out the nitration of the 3,4-dichlorotoluene with nitronium salts which can be employed as such, for example as nitronium tetrafluoborate, or can be produced from nitrogen oxides and suitable acids, such as dinitrogen pentoxide and sulphuric acid.

The sulphuric acid and nitric acid are preferably employed in a form which is as anhydrous as possible (for example in the form of 98% strength sulphuric acid and nitric acid or monohydrate).

Preferably, the customary, easily handled mixtures of concentrated sulphuric acid and $SO_3$, which contain 20 or 65% by weight of $SO_3$, are employed as oleum.

Using the process according to the invention, it is not necessary to carry out the nitration with a large excess of nitrating reagent. It suffices to employ the nitric acid or the nitronium salts in the amount theoretically required for the dinitration, namely 2 mols, relative to dichlorotoluene. Of course it is also possible to employ a larger amount of nitric acid or of nitronium salts. In practice, about 2 to 4 mols, preferably 2.05 to 3.5 mols, of nitric acid or nitronium salts, relative to 1 mol of dichlorotoluene, are employed.

The amount of sulphuric acid or oleum used for the dinitration can be varied within wide ranges and can easily be established by a preliminary experiment. It depends, above all, on the water content of the sulphuric acid employed and/or nitric acid employed, and on the $SO_3$ content of the oleum used.

The reduction, with partial or complete splitting-off of the chlorine atoms, which follows the dinitration of the 3,4-dichlorotoluene can, according to the process of the invention, be carried out in the presence of an organic solvent and/or diluent which is inert under the reaction conditions and/or in the presence of water, with optionally carrier-supported Raney catalysts or noble metals in elementary or chemically bonded form, if appropriate in the presence of a suitable acceptor for hydrochloric acid, or with base metals in an acidic medium.

Inert organic solvents and/or diluents which can be employed in the reduction are aliphatic, cycloaliphatic, aromatic or araliphatic hydrocarbons with up to 20 C atoms, preferably 6 to 15 C atoms, such as hexane, heptane, octane, dodecane, cyclohexane, decalin, benzene, toluene, xylene and their isomers; aliphatic, cycloaliphatic or aromatic ethers, with up to 14 C atoms, preferably with 4 to 8 C atoms, such as methyl butyl ether, tetrahydrofuran, anisole, 1,4-dioxane and their isomers; aliphatic or cycloaliphatic alcohols or phenols, with up to 12 C atoms, preferably 1 to 8 C atoms, such as methanol, ethanol, propanol, butanol, pentanol, cyclohexanol, phenol and their isomers, as well as aliphatic carboxylic acids, carboxylic acid esters or carboxylic acid amides with up to 12 C atoms, preferably with 2 to 6 C atoms, such as acetic acid, ethyl acetate, butyl acetate, dimethylformamide and dimethylacetamide.

Furthermore, it is possible to carry out the reduction in the presence of water.

Preferably, lower alcohols, such as methanol, ethanol, propanol and/or butanol as well as their isomers and/or water, are employed in the reduction.

In the reduction, the solvents and/or diluents can be employed either individually or as mixtures with one another.

The amount of the inert organic solvents and/or diluents or of the water is not critical and can vary within wide limits. The optimum amount can easily be determined by preliminary experiments.

As Raney catalysts, conventional Raney contact catalysts, such as Raney nickel, Raney nickel-iron, Raney nickel-cobalt, Raney nickel-copper or Raney cobalt can be employed in the process according to the invention. Preferably, Raney nickel catalysts are used.

As noble metals, there may be mentioned the elements of group 8 of the Mendeleef periodic table of the elements, such as ruthenium, rhodium, palladium and platinum, preferably palladium and platinum.

Examples of the chemically bonded form in which noble metals can be employed are the oxides or halides.

The noble metal catalysts can be supported on carrier materials. For this purpose, all carrier materials known per se can be employed, provided they are inert under the reaction conditions. Barium sulphate, aluminium oxides, silicates and carbon in various forms, preferably active charcoal, may be mentioned as such carriers.

Particularly when the process according to the invention is carried out continuously, it is advantageous to arrange the noble metal catalyst, on a carrier material, as a fixed bed catalyst or fluidized bed catalyst in the reaction space.

For complete splitting-off of the chlorine atoms, Raney nickel or palladium is preferably employed as the catalyst, whilst for partial dehalogenation platinum is preferably employed as the catalyst.

The catalysts which are employed for carrying out the process according to the invention retain their activity and their selectivities even on repeated use or, if the process according to the invention is carried out continuously, over long periods, and give constant high yields.

The amount of the catalysts to be employed is in general 0.01 to 30% by weight, preferably 0.3 to 20% by weight, relative to the 3,4-dichlorotoluene employed as the starting material. If a catalyst supported on a carrier is used, the amount of contact catalyst to be employed depends on the weight ratio of carrier material to catalyst, and is so chosen that the amount of the catalyst corresponds to the abovementioned amount of catalyst to be employed.

If the reduction and the dehalogenation of the dinitrodichlorotoluene are carried out catalytically with hydrogen in the presence of the Raney catalysts or noble metal catalysts described above, the process is in general carried out under hydrogen pressures of 1 to 300 bar, preferably at 2 to 200 bar.

The temperatures can at the same time vary within wide limits and depend, like the hydrogen pressure, above all on the solvent and/or diluent used for the nitration and on the particular hydrochloric acid acceptor employed. Usually, the hydrogenation is carried out at 20° to 250° C., preferably at 30° to 200° C.

In order to split off the chlorine atoms completely during the reduction of the dinitrated 3,4-dichlorotoluene, compounds which bind or buffer the hydrochloric acid liberated during the reduction are added. Examples of compounds which are suitable for this purpose are bases, such as metal oxides, hydroxides, carbonates and salts of organic acids. Thus, alkali metal oxides, alkali metal hydroxides, alkali metal carbonates, alkaline earth metal oxides, alkaline earth metal hydroxides or alkaline earth metal carbonates, such as calcium oxide, calcium hydroxide, calcium carbonate, barium oxide, barium hydroxide, sodium hydroxide, sodium carbonate, potassium hydroxide and potassium carbonate, as well as ammonia and ammonium hydroxide, and also acetates, such as ammonium acetate or sodium acetate, can be employed as acid acceptors, either individually or as mixtures with one another. The hydrochloric acid acceptors can be added to the reaction mixture either undiluted or as a solution or suspension in an inert solvent and/or diluent which is suitable for the reduction.

The agents which bind hydrochloric acid can be employed in slight deficiency or in excess, relative to the amount of hydrochloric acid formed during the dechlorination. Preferably, however, the acid-binding agents are added in about equivalent amount.

The process according to the invention can be carried out in various ways. Thus, it is possible to carry out the dinitration of the 3,4-dichlorotoluene and the reduction of the corresponding dinitro compound without intermediate isolation of the dinitrated compound, in a so-called "one-vessel process", or first to isolate the nitro compound and then to reduce the latter, in one or more stages, to 2,6-diaminotoluene or 2,6-diamino-4-chlorotoluene.

In the procedure employing intermediate isolation of the 3,4-dichloro-2,6-dinitrototluene, the procedure followed can be, for example, to nitrate the 3,4-dichlorotoluene at temperatures of about 30° to 40° C. in a dodecane isomer mixture with a sulphuric acid/nitric acid mixture and to isolate the dichlorodinitrotoluene, for example by filtering the reaction mixture. After phase separation, the organic solvent can be recycled completely and the waste acid (the mixture of sulphuric acid, nitric acid and water) formed during the nitration can be recycled at least partially, if appropriate after addition of water-binding agents, such as oleum. This recycling of the solvents and/or diluents and of the waste acid can save substantial amounts of solvent and/or diluent as well as of sulphuric acid. Furthermore, recycling of the product-saturated solvent and/or diluent makes it possible to isolate the nitration product virtually quantitatively, relative to dichlorotoluene employed, in solid form.

If very high purity is required, the 3,4-dichloro-2,6-dinitrotoluene can be obtained in a purity of better than 99% by crystallization, redissolving and reprecipitating or, preferably, extractive boiling with a suitable solvent, for example methanol.

The nitration of the 3,4-dichlorotoluene can be carried out in various ways. Thus, for example, it is possible to take the material to be nitrated, together with the inert organic solvent and/or diluent and to add the nitrating agent, or to take the nitrating agent and to add the product to be nitrated, either undiluted or dissolved or suspended in an inert organic solvent and/or diluent. Furthermore, the nitrating agent and the material to be nitrated, dissolved or suspended in a solvent and/or diluent, can be added simultaneously to already partially or completely nitrated product. Preferably, the nitration is carried out by taking the product to be nitrated, together with the inert organic solvent and/or diluent, and adding the nitrating agent.

Using the process according to the invention, the 3,4-dichloro-2,6-dinitrotoluene can, as mentioned previously, be reduced to 2,6-diaminotoluene or to 2,6-diamino-4-chlorotoluene in one or more stages.

In the one-stage procedure, the 3,4-dichloro-2,6-dinitrotoluene is preferably reduced catalytically with Raney catalysts or with noble metal catalysts in the presence of organic solvents and/or diluents which are inert under the reaction conditions, and, if appropriate, in the presence of suitable hydrochloric acid acceptors.

Thus, for example, 2,6-diaminotoluene is obtained in good yields if 3,4-dichloro-2,6-dinitrotoluene is hydrogenated with Raney nickel in isopropanol in the presence of calcium oxide at temperatures of 50° to 150° C. and at a hydrogen pressure of 10 to 30 bar.

The one-stage reduction to 2,6-diamino-4-chlorotoluene also succeeds with good yields and good purities if, for example, 3,4-dichloro-2,6-dinitrotoluene is reduced with platinum in the presence of lower alcohols at temperatures of about 100° to 130° C. and at a hydrogen pressure of about 5 to 15 bar. The addition of a hydrochloric acid acceptor is not absolutely essential under these reaction conditions.

In the multi-stage procedure, the 3,4-dichloro-2,6-dinitrotoluene is first reduced to the corresponding diamino compound and the latter—which can, if appropriate, be isolated as an intermediate stage—is then partially or completely dehalogenated. Using the process according to the invention, the complete dehalogenation of the diaminotoluenes is carried out with addition of compounds which can bind or buffer the hydrochloric acid liberated when splitting off the chlorine.

In this multi-stage process, the reduction of the nitro groups can be carried out catalytically with Raney catalysts, for example Raney nickel, in the presence of hydrogen or hydrazine, or with noble metal catalysts, such as platinum or palladium, in the presence of hydrogen and of a solvent and/or diluent which is inert under the reaction conditions. Other customary methods for the reduction of nitro groups are however also possible, such as reduction with base metals, for example with iron, zinc or tin.

If it is desired, for example, to isolate the diaminodichlorotoluene as an intermediate product before splitting off the chlorine atoms, the nitro groups of the dinitrodichlorotoluene are preferably reduced with Raney nickel, platinum or palladium, particularly preferentially with platinum, in the presence of alcohols. In doing so, the temperature and hydrogen pressure are so chosen that the splitting-off of chlorine is as far as possible suppressed. In order to repress the dehalogenation as far as possible, it can furthermore be advantageous to add to the reaction mixture catalytic amounts of catalyst regulators, namely, for example, substances which have a basic reaction, such as morpholine, calcium carbonate and/or calcium oxide, as well as lead compounds, such as lead acetate, or sulphur compounds such as bis-(2-hydroxyethyl)-sulphide.

The optimum amount of catalyst regulator to be added, as well as the optimum temperature and optimum hydrogen pressure, can easily be determined by preliminary experiments.

The catalytic hydrogenation of 2,6-dinitro-3,4-dichlorotoluene with platinum at 45° C. under a hydrogen-pressure of 10 bar in the presence of catalytic amounts of morpholine gives, for example, the 2,6-diamino-3,4-dichlorotoluene in high yields and high purity.

In the reduction of the dichlorodinitrotoluene without intermediate isolation of the corresponding dichlorodiaminotoluene, the procedure followed is, for example, to hydrogenate the dinitro compound under a slight excess pressure of hydrogen (about 1 to 15 bar), and at temperatures of about 20° to 60° C., in the presence of Raney nickel or palladium, preferably in alcohols or alcohol/water mixtures. Under these hydrogenation conditions, splitting-off of chlorine takes place to only a slight degree, so that corrosion problems need not be feared. However, in order to be able to suppress the splitting-off of chlorine even further it is possible, as mentioned previously, also to add catalyst regulators to the reaction mixture.

For complete hydrogenolysis of the chlorine atoms, compounds which bind or buffer the hydrochloric acid liberated in the hydrogenation are added, according to the process of the invention, to the diaminodichlorotoluene solution or suspension. These can be added undiluted, or as a solution or suspension in an inert solvent and/or diluent suitable for the hydrogenation, to the reaction mixture. The solvent and/or diluent employed, in particular the base employed, determine the optimum temperature and pressure parameters for complete splitting-off of chlorine. This means that there is a wide spectrum of temperature and pressure parameters under which 2,6-diaminotoluene can be obtained in good yields and good quality.

If, for example, a hydrogenation installation only suitable for the low pressure range is available, it is advisable to employ, in particular, alkali metal and/or alkaline earth metal hydroxides and/or oxides as acid acceptors. Thus, for example, the complete dehalogenation of diaminodichlorotoluene in alcoholic or aqueous-alcoholic solution or suspension can, after addition of equimolar amounts of sodium hydroxide solution, be carried out even under a low hydrogen pressure (about 2 to 10 bar) and at temperatures below 50° C., for example as low as 45° C. If higher temperatures are used, the splitting-off of chlorine accelerates. For example, it proceeds more than twice as rapidly at 80° C. than at 50° C.

If, on the other hand, a hydrogenation apparatus is available which permits carrying out the reaction at high hydrogen pressures, the dehalogenation can also be carried out at pressures above 10 bar (for example 10 to 200 bar) and at higher temperatures, for example 50° to 200° C.

If only a partial dehalogenation of the 3,4-dichloro-2,6-dinitrotoluene to 2,6-diamino-4-chlorotoluene is to be carried out, the partial splitting-off of chlorine can be controlled by addition of compounds such as morpholine, ammonium chloride or ammonium acetate, and the selectivity of the dehalogenating agent can thereby be substantially improved.

In such cases, the hydrogenation conditions depend on the nature of the compounds added. Depending on the nature of the compound, mild or drastic hydrogenation conditions should be chosen to achieve partial splitting-off of chlorine. If, for example, morpholine is added to the reaction mixture, hydrogenation can be carried out under a hydrogen pressure of about 3 to 7 bar and at temperatures of about 80° to 100° C. If ammonium chloride is added, the partial dehydrogenation can be carried out at 10 to 30 bar and at temperatures of 70° to 110° C., whilst, for example, if ammonium acetate is added a hydrogen pressure of about 150 to 200 bar and temperatures of about 130° to 170° C. are advantageous.

The partial dechlorination of the 3,4-dichloro-2,6-dinitrotoluene can also be carried out with base metals in an acidic medium, instead of with Raney catalysts or noble metal catalysts. In that case, for example, the dichlorodinitro compound is reduced, and partially dehalogenated, in aqueous hydrochloric acid, using iron, zinc or tin.

The partial dehalogenation of 2,6-diamino-3,4-dichlorotoluene to 2,6-diamino-4-chlorotoluene can be carried out under the same conditions as described before for the partial dehalogenation of 3,4-dichloro-2,6-dinitrotoluene.

The reduction of the 3,4-dichloro-2,6-dinitrotoluene to 2,6-diaminotoluene or 2,6-diamino-4-chlorotoluene can either be carried out in one autoclave only, in which case it is advantageous to wash the catalyst alkali-free after having carried out the dechlorination and to recycle it to the hydrogenation process, or in two separate reactors, in which case only the reduction of the nitro groups is carried out in one reactor, whilst in the other exclusively the dehalogenation is carried out, the catalyst being recycled in the case of both reactions. When two separate reactors are used, washing the catalyst alkali-free before recycling it is dispensed with.

In the nitration, subsequent reduction and partial or complete dehalogenation of 3,4-dichlorotoluene to be carried out in a so-called "one-vessel process", the procedure followed is generally that the nitration is carried out in the presence of an inert organic solvent and/or diluent, for example a dodecane isomer mixture and after separating off the waste acid the nitration product, dissolved in the organic solvent, is mixed with catalyst and, if appropriate, with one of the additives previously mentioned, and the reduction and dehalogenation are then carried out as described above.

The working up of the reaction mixture obtained in various ways can be carried out in the usual manner. If the reaction has been carried out in the presence of additives which bind hydrochloric acid, it is possible, for example, first to remove the catalyst, and any salts which have precipitated, from the reaction mixture by filtration and then, after removing the inert organic solvent and/or diluent, to separate the 2,6-diaminotoluene or the 2,6-diamino-4-chlorotoluene in a known manner from the salt which has remained. For this purpose it is possible, for example, to add to the reaction mixture a solvent in which the diaminotoluene is soluble, whilst the salt is not, or to dissolve the salt in water and extract the 2,6-diaminotoluene with a suitable solvent, or to crystallize the diaminotoluene from the aqueous phase.

The process according to the invention can be carried out either continuously or discontinuously.

Using the process according to the invention, the optionally p-chlorine-substituted 2,6-diaminotoluene is obtainable in a simple manner, in high yields and good purities. Virtually no side reactions are observed. Accordingly, industrially involved and expensive crystallization and purification operations are dispensed with. Because of the mild nitration conditions and because of the possibility of recycling and reusing the solvent obtained after the nitration, and, if desired, the waste acid as well as the catalyst employed, the process according to the invention proves to be a process which is easily operated both safely and without pollution of the environment.

2,6-Diaminotoluene and 2,6-diamino-4-chlorotoluene are, for example, valuable intermediates for the preparation of diisocyanates and polyurethanes (U.S. Pat. No. 3,203,931); 2,6-diaminotoluene is furthermore used to prepare dyestuffs and antioxidants (U.S. Pat. No. 2,765,348).

The examples which follow are intended to illustrate the process according to the invention without however restricting it to these examples.

EXAMPLES

Example 1

Nitrating acid consisting of 643 g (10.2 mols) of 98% strength nitric acid and 3,064 g of 98% strength sulphuric acid is added dropwise, at 0° C., to 644 g (4 mols) of 3,4-dichlorotoluene in 1,200 ml of methylene chloride. The temperature is then raised to 40° C. and stirring is continued until complete conversion to dichlorodinitrotoluene has taken place. After phase separation, the waste acid is extracted with methylene chloride and the organic phases are combined and washed neutral with sodium carbonate solution. After driving off the solvent, and drying, 997 g of crystalline residue, of melting point 90° to 91° C., remain.

Yield, relative to 3,4-dichlorotoluene: 99.3% of theory; purity (gas chromatography): 95.9% of 3,4-dichloro-2,6-dinitrotoluene; 3.9% of 4,5-dichloro-2,3-dinitrotoluene.

To remove the small amount of dinitro isomers, the crude product can be suspended in 2,290 ml of methanol and kept at the reflux temperature for 30 minutes. After the mixture has cooled to room temperature, the crystal slurry is filtered off, rinsed with 498 ml of ice-cold methanol and dried. Yield 924 g, melting point 92° to 93° C., purity (gas chromatography) 99.5%.

Example 2

Mixed acid consisting of 164 g (2.55 mols) of 98% strength nitric acid and 860 g of monohydrate is added dropwise to 200 g (1.24 mols) of 3,4-dichlorotoluene in 1,400 ml of technical-grade isododecane at 33° to 36° C. Stirring is continued, at the same temperature, until complete conversion has taken place. The reaction mixture is run into 2,400 ml of cold water. After filtering off, the residue is rendered neutral with sodium carbonate and is freed from solvent by means of steam. The yield of dichloro-dinitro-toluene, including the amount present in the isododecane mother liquor, is 301 g.

Purity (gas chromatography): 94.4% of 3,4-dichloro-2,6-dinitrotoluene; 4.5% of 4,5-dichloro-2,3-dinitrotoluene.

The nitration product, containing 4.5% of 4,5-dichloro-2,3-dinitrotoluene is suspended in 2,150 ml of methanol and 8.5 g of $CaCO_3$ and 60 g of Raney nickel (moist with water) are added thereto, in an autoclave equipped with a stirrer. After flushing the autoclave with argon, the reduction of the nitro groups is carried out in the presence of hydrogen, under a total pressure of 4 bar and at a temperature of 50° C., the pressure being kept constant by forcing in hydrogen. The splitting-off of chlorine takes place at the same pressure, and a temperature of 80° C., after having pumped in 96 g (2.4 mols) of NaOH in 700 ml of water. To work up the mixture, the catalyst is filtered off and the alcohol is distilled off under normal pressure. The product is filtered off after having cooled; residual amounts of product are isolated by extraction with methylene chloride. After distillation at 45 mbar/185° C., 136.5 g (90.2% of theory, relative to 3,4-dichlorotoluene) of colourless 2,6-diaminotoluene, of 97.0% purity (gas chromatography), are obtained.

If 99.5% pure 3,4-dichloro-2,6-dinitrotoluene, prepared according to Example 1, is employed, the purity of the 2,6-diamono-toluene, obtained analogously to the above description, is 99.7%, the yield being as before.

Example 3

161 g (1 mol) of 3,4-dichlorotoluene, of 99.5% purity, are diluted with 1,160 ml of technical-grade isododecane and a mixed acid prepared from 206 g (3.2 mols) of 98% strength nitric acid and 770 g of 98% strength sulphuric acid is added, starting at room temperature, in such a way that the temperature does not rise above 33° to 36° C. The mixture is then stirred for a further hour, after which it is thoroughly suction-drained. The crude product, isolated by filtration, is washed with water and then freed from adhering isododecane by flushing with steam, sodium carbonate being added in order to remove residual amounts of acid.

The total yield is 99.3% of theory, based on 3,4-dichlorotoluene and the selectivity for 3,4-dichloro-2,6-dinitrotoluene is 95.6%. If the isododecane mother liquor is recycled ten times, the amount of dichlorodinitro-toluene isolated by filtration averages 98.5% of theory.

Example 4

161 g (1 mol) of 3,4-dichlorotoluene in 1,000 ml of isododecane are nitrated with a mixed acid, prepared from 193 g (3 mols) of 98% strength nitric acid and 246 g of 65% oleum, at 30° to 33° C. After working up by suction filtration of the reaction mixture, dichloro-dinitro-toluene is obtained in a yield of 94.4% of theory, relative to 3,4-dichlorotoluene.

Example 5

A mixed acid of 144 g (2.25 mols) of nitric acid (98% strength) and 490 g of monohydrate is added dropwise to 161 g (1 mol) of 3,4-dichlorotoluene in 1,000 ml of technical-grade isododecane at 33° to 35° C. Stirring is then continued at the same temperature for 2 hours. Thereafter, the nitration product which has precipitated is filtered off directly and the waste acid is separated from the filtrate. The filter cake and mother liquor are worked up as described in Example 2. Together with the amount obtained from the isododecane phase, a yield of dichlorodinitrotoluene of 98.5% is achieved. The selectivity is 92.2%.

Example 6

50.2 g (0.2 mol) of 3,4-dichloro-2,6-dinitrotoluene are hydrogenated in 200 ml of isopropanol with hydrogen under 10 bar total pressure in the presence of 11.2 g of CaO and 5 g of Raney nickel (moist with water) in an autoclave, whilst stirring at 50° C. After the absorption of hydrogen has slowed down, the temperature is raised to 150° C. and the pressure to 30 bar. The content of 2,6-diaminotoluene in the hydrogenation product is 87.2%.

Example 7

25.1 g (0.1 mol) of 3,4-dichloro-2,6-dinitrotoluene are hydrogenated with hydrogen under 15 bar total pressure in the presence of 200 ml of methanol, 5 g of Raney nickel (moist with water) and 0.7 g of $CaCO_3$, at a temperature of 50° C., until dichlorodinitrotoluene is no longer detectable. After addition of 8.4 g (0.21 mol) of NaOH in 100 ml of methanol, the product is dehalogenated under the same conditions. The yield of 2,6-diaminotoluene is 95.6%.

Example 8

The procedure followed is analogous to Example 7, but using 3 g of 1% strength palladium on Eponit® charcoal, as the catalyst. Yield of 2,6-diaminotoluene: 94.7%.

Example 9

15.6 g (0.1 mol) of 2,6-diamino-4-chlorotoluene, prepared according to Example 11, in 250 ml of methanol, are mixed with 5 g of Raney nickel (moist with water) and 9 g (0.11 mol) of sodium acetate and dehalogenated at 100° C. with hydrogen under a total pressure of 50 bar. Content of 2,6-diaminotoluene in the hydrogenation product: 88.1%.

Example 10

19.1 g (0.1 mol) of 2,6-diamino-3,4-dichlorotoluene, in 500 ml of isopropanol, are dehalogenated with hydrogen under a total pressure of 50 bar in the presence of 3.1 g of 1% strength palladium on charcoal and 6.2 g (0.11 mol) of CaO, at 120° C. Yield of 2,6-diaminotoluene: 91.2%.

Example 11

25.1 g (0.1 mol) 3,4-dichloro-2,6-dinitrotoluene are hydrogenated with hydrogen under 10 bar total pressure in the presence of 200 ml of methanol, 2 g of 1% strength platinum on Eponit® charcoal and 0.75 g morpholine at a temperature of 45° C. After 30 minutes the theoretical amount of hydrogen has been absorbed. Then, after 2 hours the catalyst is filtered off and the solvent is distilled off. It remains 19.1 g of crystals with a melting point of 119°–120° C. and a content of 2,6-diamino-3,4-dichlorotoluene of 98%.

50 ml of methanol, 12.3 g (0.22 mol) of CaO and 2 g of 1% strength platinum of Eponit® charcoal are first introduced into an autoclave and a solution of 19.1 g (0.1 mol) of 2,6-diamino-3,4-dichlorotoluene in 200 ml of methanol is then pumped in at a rate of 2 ml/min, and hydrogenated. The total pressure in the autoclave is 120 bar and the temperature 180° C.

After separation from the catalyst, the reaction mixture is completely freed from the solvent and from the water of reaction, the residue which remains is taken up in dry methanol, undissolved salt is filtered off and the methanol is removed in vacuo.

2,6-Diamino-4-chlorotoluene is obtained in a yield of 91.7% of theory, and in a purity (gas chromatography) of 96.1%; melting point: 75° to 77° C.

Example 12

19.1 g (0.1 mol) of 2,6-diamino-3,4-dichlorotoluene are hydrogenated with hydrogen under a total pressure of 180 bar in an autoclave, in the presence of 500 ml of methanol, 15.4 g (0.2 mol) of ammonium acetate and 2 g of 1% strength platinum on medicinal charcoal, at 150° C. After separating off the catalyst by filtration and removing the solvent, the residue if taken up in water and the mixture is rendered neutral with sodium hydroxide solution and extracted with methylene chloride. 2,6-Diamino-4-chlorotoluene is obtained in a yield of 97.1% of theory; the purity is 95.3%.

Example 13

The procedure followed is analogous to Example 12, but instead of the ammonium acetate 10.7 g (0.2 mol) of ammonium chloride are added. Partial dehalogenation is effected with hydrogen under a total pressure of 20 bar, at 90° C. 2,6-Diamino-4-chlorotoluene is obtained in a purity of 98% and a yield of 91% of theory.

Example 14

25.1 g (0.1 mol) of 3,4-dichloro-2,6-dinitrotoluene are mixed with 200 ml of isopropanol and 2 g of 1% strength platinum on charcoal and hydrogenated with hydrogen under a total pressure of 10 bar in an autoclave, equipped with a stirrer, at 120° C. When the absorption of hydrogen has slowed down, the pressure is raised to 50 bar under the same temperature conditions, and the pressure maintained at these conditions until the partial dechlorination has taken place completely. Working up takes place analogously to Example 12. The content of 2,6-diamino-4-chlorotoluene in the hydrogenation product is 97.4%.

Example 15

50 mg of platinum oxide are added to 19.1 g (0.1 mol) of 2,6-diamino-3,4-dichlorotoluene, 10.7 g (0.2 mol) of ammonium chloride and 500 ml of water in an autoclave. The reaction is carried out at 90° C. with hydrogen under a total pressure of 20 bar. After separating off the catalyst by filtration, the mixture is rendered neutral with sodium hydroxide solution and extracted with methylene chloride. The content of 2,6-diamino-4-chlorotoluene in the hydrogenation product is 89%.

Example 16

25.1 g (0.1 mol) of 3,4-dichloro-2,6-dinitrotoluene, 25.2 g (0.45 mol) of iron powder in 50 ml of water are warmed to the boiling point. 100 ml of concentrated hydrochloric acid are then added dropwise and the reaction mixture is kept under reflux until the 3,4-dichloro-2,6-dinitrotoluene has been completely converted to 2,6-diamino-3,4-dichlorotoluene. After addition of a further 16.8 g (0.3 mol) of iron, dehalogenation is effected at the reflux temperature.

After having been rendered neutral, and separated from the iron sludge, the mixture is extracted with methylene chloride. The reaction product contains 88.9% of 2,6-diamino-4-chlorotoluene.

What is claimed is:

1. A process for the preparation of 2,6-diaminotoluene, which comprises dinitrating 3,4-dichlorotoluene with 2-4 mols of dinitrating agent per mol of 3,4-dichlorotoluene in the presence of an inert, water immiscible organic solvent at a temperature of (−10° to +100° C.) 0°-40° C. and thereafter reducing the so-nitrated compound in the presence of an inert organic solvent and splitting off the chlorine atom whereby to form 2,6-diaminotoluene.

2. A process according to claim 1, wherein the dinitration is carried out in an aliphatic or cycloaliphatic hydrocarbon with 5 to 20 carbon atoms or a halogenated aliphatic hydrocarbon with 1 to 3 carbon atoms.

3. A process according to claim 1, wherein the dinitration is effected using as a dinitrating agent, a mixture of sulfuric acid and nitric acid, a mixture of oleum and nitric acid, or a nitronium salt.

4. A process according to claim 1, wherein the dinitrated compound is reduced in an aliphatic, cycloaliphatic, aromatic or araliphatic hydrocarbon with up to 20 carbon atoms or an aliphatic, cycloaliphatic or aromatic ether with up to 14 carbon atoms or a phenol, an aliphatic or cycloaliphatic alcohol having up to 12 carbon atoms or an aliphatic carboxylic acid, carboxylic acid ester or carboxylic acid amide with up to 12 carbon atoms.

5. A process according to claim 1, wherein the reduction is carried out with hydrogen catalytically in the presence of an optionally carrier-supported Raney catalyst or noble metal of group 8 of the periodic table of elements or with a base metal in an acidic medium.

6. A process according to claim 1, wherein the chlorine atom or atoms is split off by carrying out the reduction in the presence of a Raney nickel or palladium catalyst.

7. A process for the preparation of p-chlorine-substituted 2,6-diaminotoluene which comprises dinitrating 3,4-dichlorotoluene employing 2 to 4 mols of dinitrating agent per mol of 3,4-dichlorotoluene in the presence of an inert water immiscible organic solvent at a temperature of (−10° to +100° C.) 0° to 40° C. and thereafter reducing the so-dinitrated compound in the presence of an inert organic solvent and splitting off one chlorine whereby to form p-chlorine-substituted 2,6-diaminotoluene.

8. A process according to claim 7, wherein the removal of at least one of the chlorine atoms is carried out in the presence of platinum as catalyst.

9. A process according to claim 1, wherein the dinitrated compound is reduced catalytically under a hydrogen pressure of 1 to 300 bars at a temperature of 20° to 250° C.

10. A process according to claim 1, wherein the reduction of the dinitrated compound is carried out in the presence of a metal oxide, metal hydroxide, metal carbonate or salt of an organic acid whereby the chlorine atoms are completely removed from the dinitrated compound while the same is reduced to form 2,6-diaminotoluene.

11. A process according to claim 1, wherein the reduction of the dinitrated compound is carried out in the presence of water.

12. A process according to claim 7, the reduction is carried out in the presence of morpholine, ammonium chloride or ammonium acetate.

13. A process according to claim 1, wherein the reduction of the dinitrated compound is carried out following intermediate isolation of the dinitrated compound.

14. A process according to claim 1, wherein reduction of the dinitrated compound is carried out without isolation of the dinitrated compound from its reaction mixture.

15. A process according to claim 7, wherein the reduction of the dinitrated compound is carried out under conditions in which removal of the chlorine atoms from the benzene nucleus of the dinitrated toluene does not occur and thereafter one of the chlorine atoms is removed from the resultant 2,6-diamino-3,4-dichlorotoluene.

16. A process according to claim 1, wherein the reduction of the dinitro compound is carried out under conditions in which removal of chlorine atoms from the benzene nucleus of the dinitrated toluene does not occur and thereafter both of the chlorine atoms are removed by contacting the 2,6-diamino-3,4-dichlorotoluene which forms with hydrogen in the presence of a compound which binds or buffers hydrochloric acid.

17. A process according to claim 7, wherein the dinitrated 3,4-dichlorotoluene is catalytically reduced under hydrogen pressure of 1 to 3 bars at a temperature of 20° to 250° C.

18. A process according to claim 7, wherein the reduction of the dinitrated compound is carried out following intermediate isolation of the dinitrated compound.

19. A process according to claim 7, wherein the reduction of the dinitrated compound is carried out without isolation of the dinitrated compound from its reaction mixture.

20. A process for the preparation of 2,6-diaminotoluene which comprises dinitrating 3,4-dichlorotoluene employing 2 to 4 mols of dinitrating agent per mol of 3,4-dichlorotoluene in the presence of an inert water immiscible organic diluent at a temperature of (−10° to +100° C.) 0° to 40° C. and thereafter reducing the so-nitrated compound in the presence of an inert organic solvent and splitting off the chlorine atoms whereby to form 2,6-diaminotoluene.

21. A process for the preparation of 2,6-diaminotoluene which comprises dinitrating 3,4-dichlorotoluene employing 2 to 4 mols of dinitrating agent per mol of 3,4-dichloro-toluene in the presence of an inert water immiscible organic solvent at a temperature of (−10° to +100° C.) 0° to 40° C. and thereafter reducing the so-dinitrated compound in the presence of an inert organic diluent and splitting off the chlorine atom whereby to form 2,6-diaminotoluene.

22. A process for the preparation of 2,6-diaminotoluene which comprises dinitrating 3,4-dichlorotoluene employing 2 to 4 mols of dinitrating agent per mol of 3,4-dichlorotoluene in the presence of an inert water immiscible organic solvent at a temperature of (−10° to +100° C.) 0° to 40° C. and thereafter reducing the so-dinitrated compound in the presence of water and splitting off the chlorine atom whereby to form 2,6-diaminotoluene.

23. A process for the preparation of p-chlorine-substituted 2,6-diaminotoluene which comprises dinitrating 3,4-dichlorotoluene employing 2 to 4 mols of dinitrating agent per mol of 3,4-dichlorotoluene in the presence of an inert water immiscible diluent at a temperature of (−10° to +100° C.) 0° to 40° C. and thereafter reducing the so-dinitrated compound in the presence of an inert organic solvent and splitting off a chlorine atom to form p-chlorine-substituted 2,3-diaminotoluene.

24. A process for the preparation of 2,6-diaminotoluene which comprises dinitrating 3,4-dichlorotoluene employing 2 to 4 mols of dinitrating agent per mol of 3,4-dichlorotoluene in the presence of a inert water immiscible organic solvent at a temperature of (−10° to +100° C.) 0° to 40° C. and thereafter reducing the so-dinitrated compound in the presence of an inert organic diluent and splitting off the chlorine atom to form p-chlorine-substituted 2,6-diaminotoluene.

25. A process for the preparation of p-chlorine substituted 2,6-diaminotoluene which comprises dinitrating 3,4-dichlorotoluene employing 2 to 4 mols of dinitrating agent per mol of 3,4-dichlorotoluene in the presence of an inert water immiscible organic solvent at a temperature of (−10° to +100° C.) 0° to 40° C. and thereafter reducing the so-dinitrated compound in the presence of water and splitting off the chlorine atom whereby to form p-chlorine-substituted 2,6-diaminotoluene.

* * * * *